United States Patent
Wittenberger et al.

(10) Patent No.: US 10,682,171 B2
(45) Date of Patent: Jun. 16, 2020

(54) VARIABLE GEOMETRY COOLING CHAMBER

(71) Applicant: Medtronic CryoCath LP, Toronto (CA)

(72) Inventors: Dan Wittenberger, L'lle-Bizard (CA); Marwan Abboud, Pierrefonds (CA); Ioana Deac, Vaudreuil-Dorion (CA)

(73) Assignee: Medtronic CryoCath LP, Toronto, Ontario (*) Notice: Subject to any disclaimer, the term of this patent is extended or adjusted under 35 U.S.C. 154(b) by 292 days.

(21) Appl. No.: 15/808,512

(22) Filed: Nov. 9, 2017

(65) Prior Publication Data

US 2018/0064482 A1    Mar. 8, 2018

Related U.S. Application Data (62) Division of application No. 11/476,928, filed on Jun. 28, 2006, now Pat. No. 9,814,511.

(51) Int. Cl.
*A61B 18/02* (2006.01)
*A61M 29/02* (2006.01)
(Continued)

(52) U.S. Cl.
CPC ........... *A61B 18/02* (2013.01); *A61M 29/02* (2013.01); *A61B 2017/00256* (2013.01);
(Continued)

(58) Field of Classification Search
CPC .................. A61B 18/02; A61B 2018/0262
See application file for complete search history.

(56) References Cited

U.S. PATENT DOCUMENTS

| | | |
|---|---|---|
| 5,071,407 A | 12/1991 | Termin et al. |
| 5,221,261 A | 6/1993 | Termin et al. |

(Continued)

FOREIGN PATENT DOCUMENTS

| | | |
|---|---|---|
| EP | 0896211 A2 | 10/1999 |
| WO | 0042932 A1 | 7/2000 |

(Continued)

OTHER PUBLICATIONS

International Search Report dated Oct. 22, 2007, for corresponding International Application No. PCT/CA2007/001075; International Filing Date: Jun. 19, 2007 consisting of 5-pages.

(Continued)

*Primary Examiner* — Kaitlyn E Smith
(74) *Attorney, Agent, or Firm* — Christopher & Weisberg, P.A.

(57) ABSTRACT

The present invention provides a medical device that may include a catheter body having proximal and distal portions, a fluid injection lumen disposed within elongate body, and a guidewire lumen disposed within the elongate body. A tip portion defining a cavity in fluid communication with the fluid injection lumen may be coupled to the distal end of the guidewire lumen, and an expandable element may be coupled to the distal portion of the catheter body and to the tip portion, such that the expandable element is in fluid communication with the fluid injection lumen. A shaping element may at least partially surround the expandable element, where the shaping element is configurable in a first geometric configuration and a second geometric configuration.

14 Claims, 8 Drawing Sheets

(51) Int. Cl.
  *A61B 17/00* (2006.01)
  *A61B 17/22* (2006.01)
  *A61B 18/00* (2006.01)
  *A61M 25/10* (2013.01)

(52) U.S. Cl.
  CPC .............. *A61B 2017/00867* (2013.01); *A61B 2017/22051* (2013.01); *A61B 2018/0022* (2013.01); *A61B 2018/0212* (2013.01); *A61B 2018/0262* (2013.01); *A61M 2025/1093* (2013.01); *A61M 2029/025* (2013.01)

(56) References Cited

U.S. PATENT DOCUMENTS

| | | | |
|---|---|---|---|
| 5,352,199 | A | 10/1994 | Tower |
| 5,409,640 | A | 4/1995 | Giret et al. |
| 5,423,771 | A | 6/1995 | Imran |
| 5,447,497 | A | 9/1995 | Sogard et al. |
| 5,496,277 | A | 3/1996 | Termin et al. |
| 5,536,252 | A | 7/1996 | Imran et al. |
| 5,603,731 | A | 2/1997 | Whitney |
| 5,653,684 | A | 8/1997 | Laptewicz et al. |
| 5,690,670 | A | 11/1997 | Davidson |
| 5,772,681 | A | 6/1998 | Leoni |
| 5,779,698 | A | 7/1998 | Clayman et al. |
| 5,799,384 | A | 9/1998 | Schwartz et al. |
| 5,836,874 | A | 11/1998 | Swanson et al. |
| 5,846,238 | A | 12/1998 | Jackson et al. |
| 5,853,411 | A | 12/1998 | Whayne et al. |
| 5,868,708 | A | 2/1999 | Hart et al. |
| 5,871,483 | A | 2/1999 | Jackson et al. |
| 5,891,136 | A | 4/1999 | McGee et al. |
| 5,910,154 | A | 6/1999 | Tsugita et al. |
| 5,925,038 | A | 7/1999 | Panescu et al. |
| 5,928,193 | A | 7/1999 | Campbell |
| 5,954,742 | A | 9/1999 | Osypka |
| 6,053,913 | A | 4/2000 | Tu et al. |
| 6,081,749 | A | 6/2000 | Ingle et al. |
| 6,221,006 | B1 | 4/2001 | Dubrul et al. |
| 6,273,886 | B1 | 8/2001 | Edwards et al. |
| 6,283,959 | B1 | 9/2001 | Lalonde et al. |
| 6,312,407 | B1 | 11/2001 | Zadno-Azizi et al. |
| 6,517,514 | B1 | 2/2003 | Campbell |
| 6,547,814 | B2 | 4/2003 | Edwin et al. |
| 6,626,861 | B1 | 9/2003 | Hart et al. |
| 6,635,068 | B1 | 10/2003 | Dubrul et al. |
| 6,748,953 | B2 | 6/2004 | Sherry et al. |
| 6,811,550 | B2 | 11/2004 | Holland et al. |
| 6,952,615 | B2 | 10/2005 | Satake |
| 6,989,009 | B2 | 1/2006 | Lafontaine |
| 7,097,643 | B2 | 8/2006 | Cornelius et al. |
| 7,497,857 | B2 | 3/2009 | Briscoe |
| 2001/0011182 | A1 | 8/2001 | Dubrul et al. |
| 2001/0012951 | A1 | 8/2001 | Bates et al. |
| 2002/0029052 | A1 | 3/2002 | Evans et al. |
| 2002/0032406 | A1 | 3/2002 | Kusleika |
| 2002/0045894 | A1 | 4/2002 | Joye et al. |
| 2002/0123765 | A1 | 9/2002 | Sepetka et al. |
| 2003/0139803 | A1 | 7/2003 | Sequin et al. |
| 2003/0236533 | A1 | 12/2003 | Wilson et al. |
| 2004/0020333 | A1 | 2/2004 | Poole et al. |
| 2004/0054367 | A1 | 3/2004 | Jimenez, Jr. et al. |
| 2004/0220560 | A1 | 11/2004 | Briscoe |
| 2004/0260333 | A1 | 12/2004 | Dubrul et al. |
| 2006/0009756 | A1 | 1/2006 | Franciscelli et al. |
| 2006/0100475 | A1 | 5/2006 | White et al. |
| 2006/0155322 | A1 | 7/2006 | Sater et al. |
| 2006/0270982 | A1 | 11/2006 | Mihalik et al. |
| 2006/0271093 | A1 | 11/2006 | Holman et al. |
| 2007/0106302 | A1 | 5/2007 | Ortiz |
| 2007/0129751 | A1 | 6/2007 | Muni et al. |
| 2008/0172084 | A1 | 7/2008 | Kusleika et al. |
| 2009/0138008 | A1 | 5/2009 | Briscoe |
| 2010/0114269 | A1* | 5/2010 | Wittenberger ......... A61B 18/02 607/105 |
| 2011/0213403 | A1 | 9/2011 | Aboytes |
| 2018/0036057 | A1* | 2/2018 | Abboud ................. A61B 18/02 |
| 2019/0151018 | A1* | 5/2019 | Mayse ............... A61B 18/1492 |

FOREIGN PATENT DOCUMENTS

| | | |
|---|---|---|
| WO | 03039338 A2 | 5/2003 |
| WO | 2008000065 A1 | 1/2008 |

OTHER PUBLICATIONS

Supplementary European Search Report dated Aug. 4, 2009, for corresponding European Application No. EP 07719991; Filing Date: Jun. 19, 2007 consisting of 6-pages.

* cited by examiner

VARIABLE GEOMETRY COOLING CHAMBER

CROSS-REFERENCE TO RELATED APPLICATION

This application is a divisional of and is related to patent application Ser. No. 11/476,928, now U.S. Pat. No. 9,815,411, filed Jun. 28, 2006, entitled VARIABLE GEOMETRY COOLING CHAMBER, the entirety of which is incorporated herein by reference.

STATEMENT REGARDING FEDERALLY SPONSORED RESEARCH OR DEVELOPMENT n/a

TECHNICAL FIELD

The present invention relates to a method and system having a variable geometry treatment element in a medical device, and in particular, to a cooling chamber of a medical device capable of having multiple geometric configurations.

BACKGROUND

Minimally invasive devices, such as catheters, are often employed for surgical procedure, including those involving ablation, dilation, and the like. In a particular situation, an ablation procedure may involve creating a series of interconnecting lesions in order to electrically isolate tissue believed to be the source of an arrhythmia. During the course of such a procedure, a physician may employ several different catheters having variations in the geometry and/or dimensions of the ablative element in order to produce the desired ablation pattern. Each catheter may have a unique geometry for creating a specific lesion pattern, with the multiple catheters being sequentially removed and replaced to create the desired multiple lesions. Exchanging these various catheters during a procedure can cause inaccuracies or movement in the placement and location of the distal tip with respect to the tissue to be ablated, and may further add to the time required to perform the desired treatment. These potential inaccuracies and extended duration of the particular procedure increase the risk to the patient undergoing treatment. Accordingly, it would be desirable to provide a single medical device having the ability to provide ablative patterns of various shapes, without the need for additional catheters or the like having a single geometric orientation, and thus, limited in the ability to provide multiple ablative patterns.

SUMMARY

The present invention advantageously provides a medical device having an elongate body defining a proximal portion, a distal portion, and a fluid injection lumen. The medical device may also include a guidewire lumen at least partially disposed within the elongate body, wherein the guidewire lumen includes a proximal end and a distal end. A tip portion may be coupled to the distal end of the guidewire lumen, where the tip portion can define a cavity in fluid communication with the fluid injection lumen.

The medical device may further include an expandable element coupled to the elongate body, the expandable element defining a proximal end and a distal end, such that the proximal end may be coupled to the distal portion of the catheter body, with the distal end being coupled to either the tip portion or the guidewire lumen. The expandable element may also be in fluid communication with the fluid injection lumen. A shaping element may be provided such that the shaping element at least partially surrounds the expandable element, with the shaping element being configurable in a first geometric configuration and a second geometric configuration.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
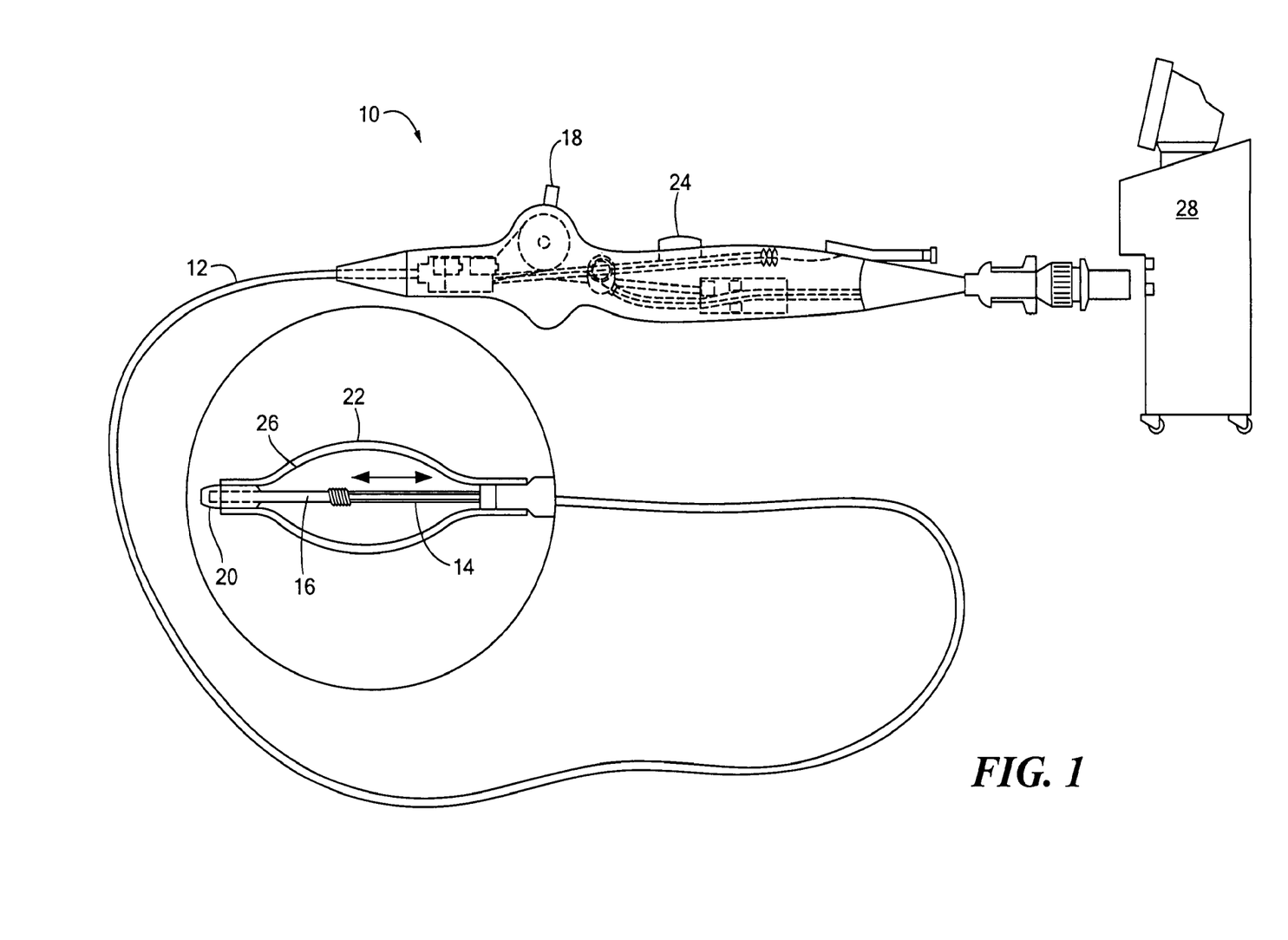
FIG. 1 illustrates an embodiment of a medical device in accordance with the present invention.
Figure 2:
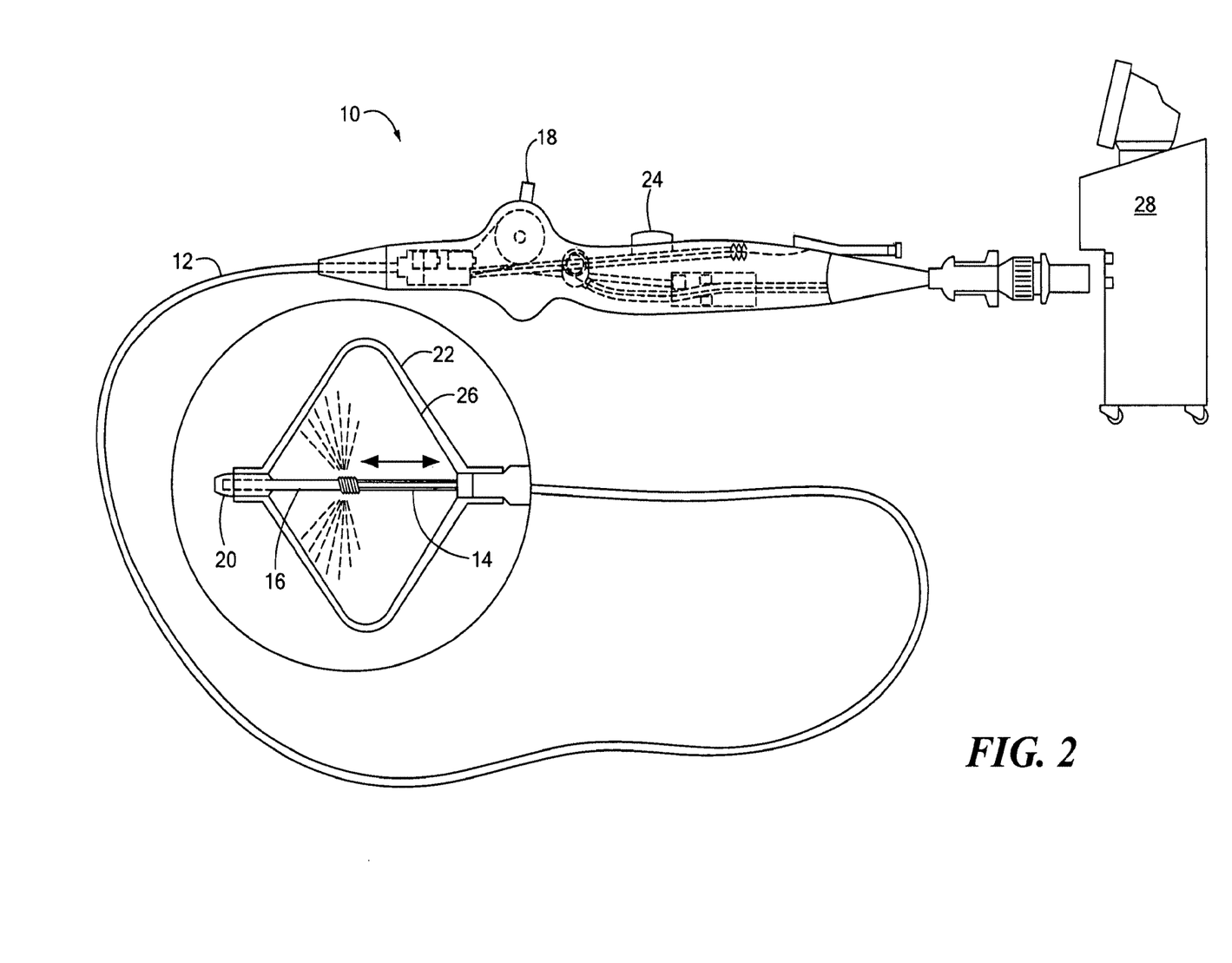
FIG. 2 shows an additional view of an embodiment of a medical device in accordance with the present invention.
Figure 3:
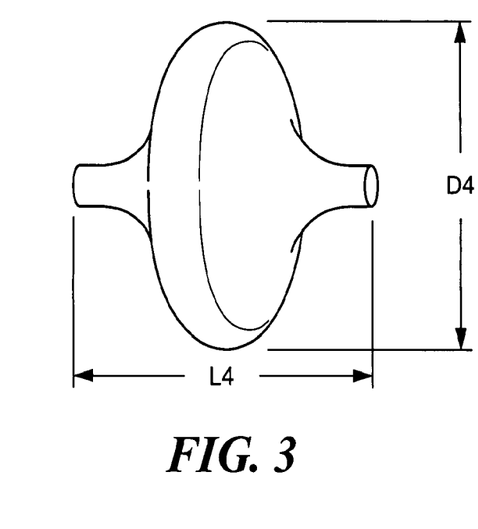
FIG. 3 shows a geometric configuration of an embodiment of a medical device in accordance with the present invention.
Figure 4:
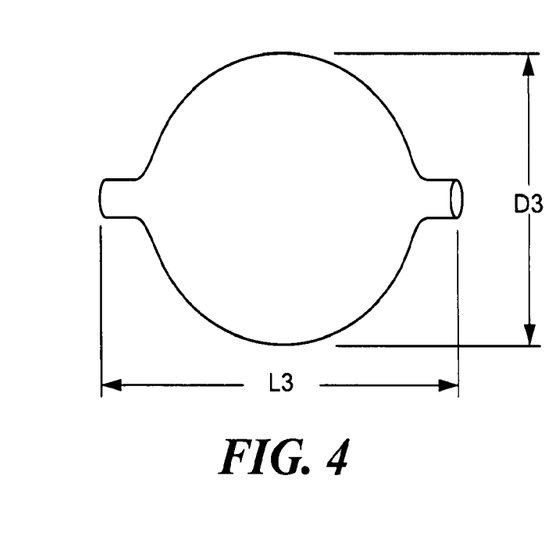
FIG. 4 depicts an additional geometric configuration of an embodiment of a medical device in accordance with the present invention.
Figure 5:
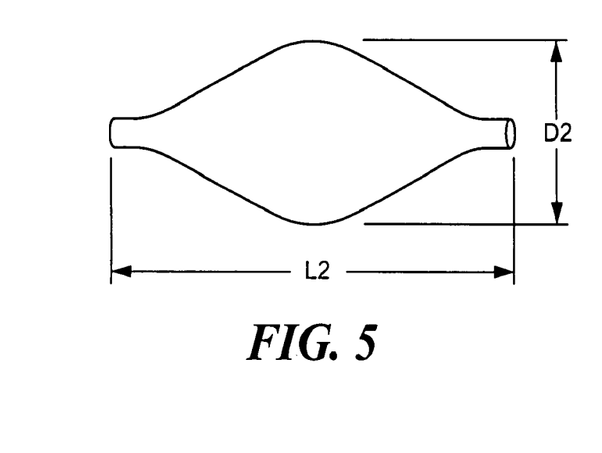
FIG. 5 illustrates another geometric configuration of an embodiment of a medical device in accordance with the present invention.
Figure 6:
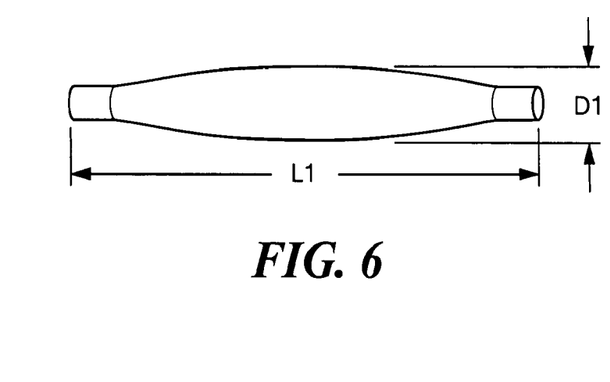
FIG. 6 shows still another geometric configuration of an embodiment of a medical device in accordance with the present invention.
Figure 7:
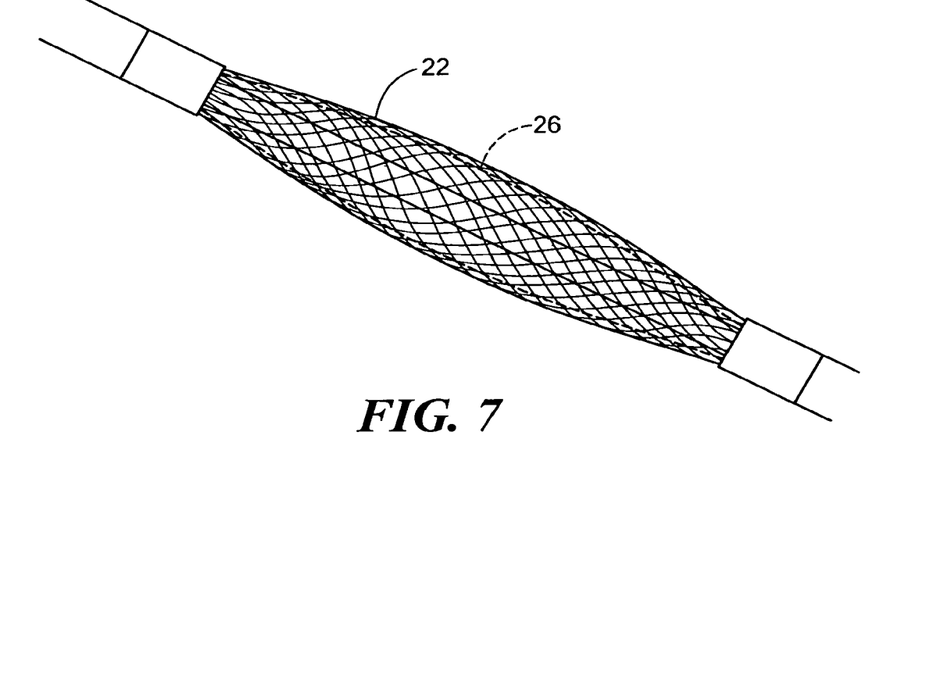
FIG. 7 depicts an additional geometric configuration of an embodiment of a medical device in accordance with the present invention.
Figure 8:
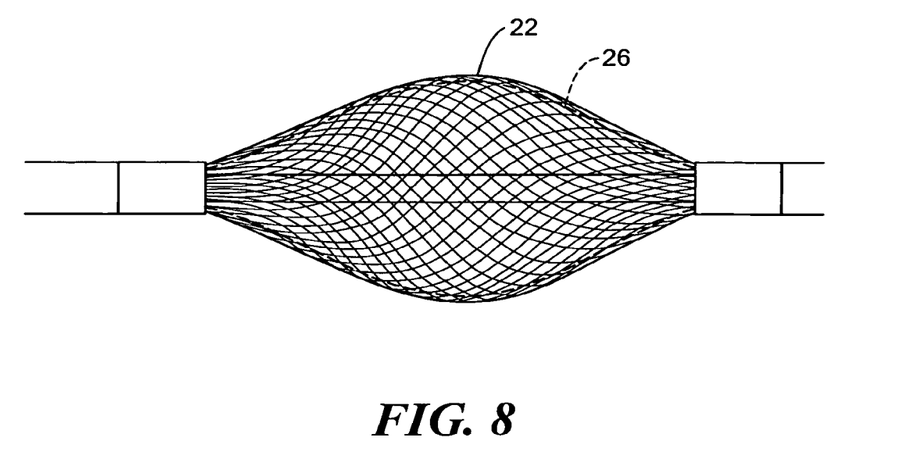
FIG. 8 illustrates another geometric configuration of an embodiment of a medical device in accordance with the present invention.
Figure 9:
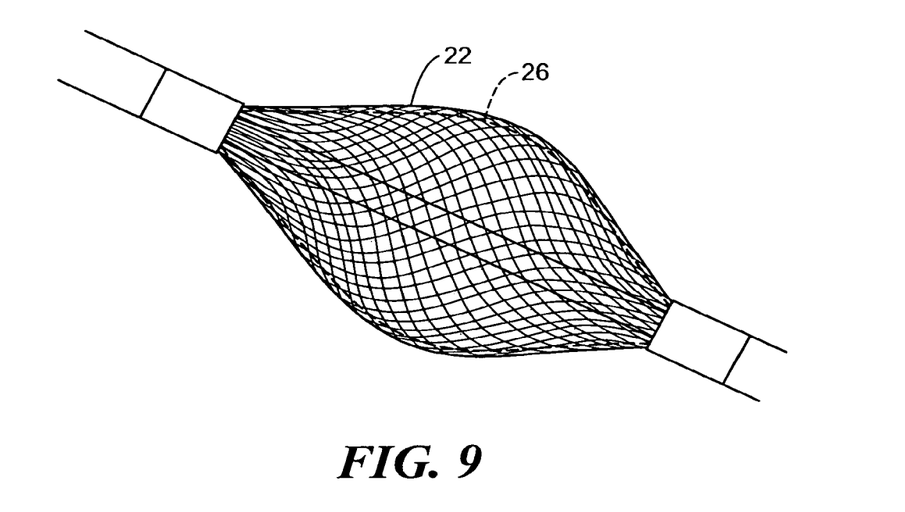
FIG. 9 shows still another geometric configuration of an embodiment of a medical device in accordance with the present invention.
Figure 10:
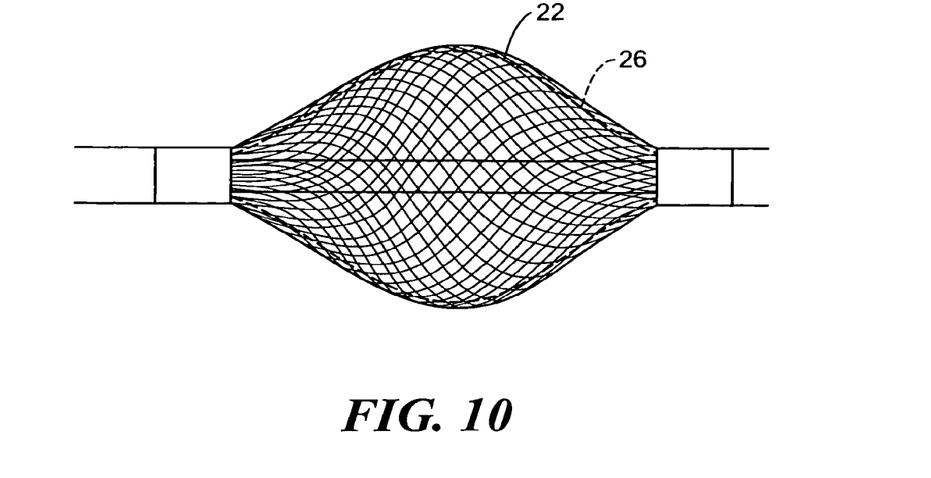
FIG. 10 shows still another geometric configuration of an embodiment of a medical device in accordance with the present invention.
Figure 11:
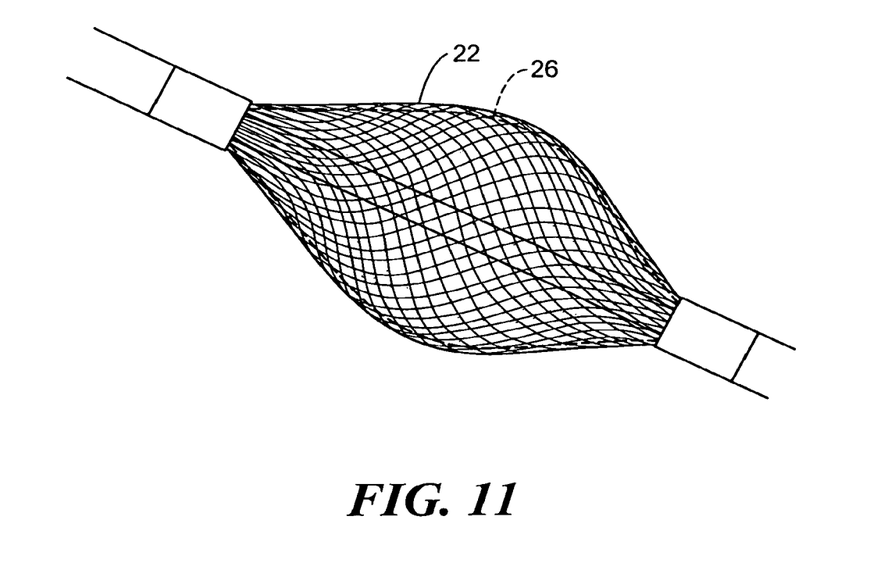
FIG. 11 depicts an additional geometric configuration of an embodiment of a medical device in accordance with the present invention.
Figure 12:
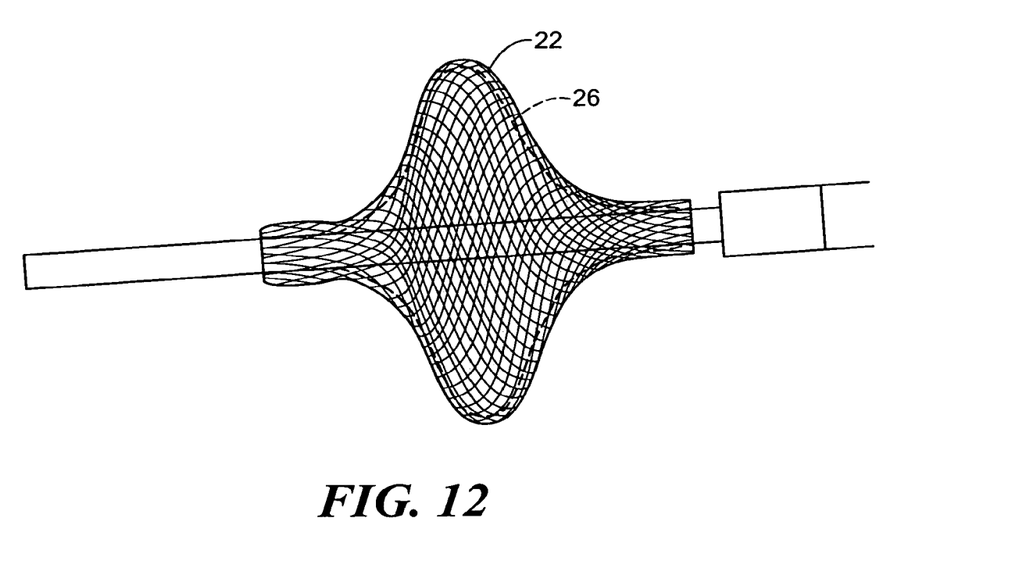
FIG. 12 illustrates another geometric configuration of an embodiment of a medical device in accordance with the present invention.
Figure 13:
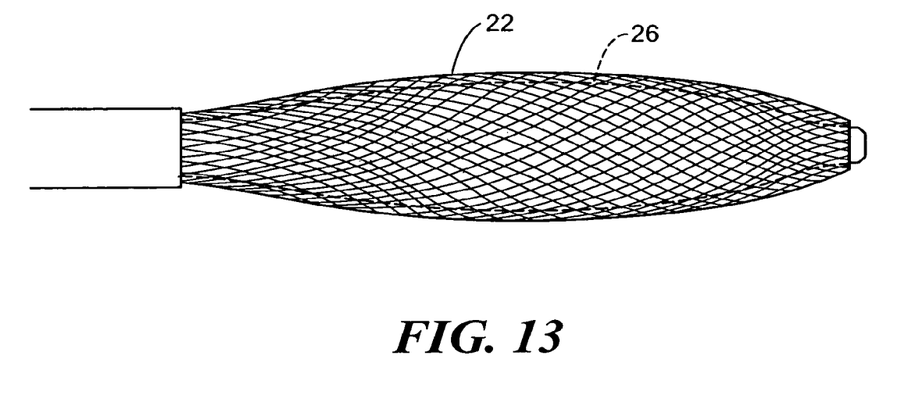
FIG. 13 shows still another geometric configuration of an embodiment of a medical device in accordance with the present invention.
Figure 14:
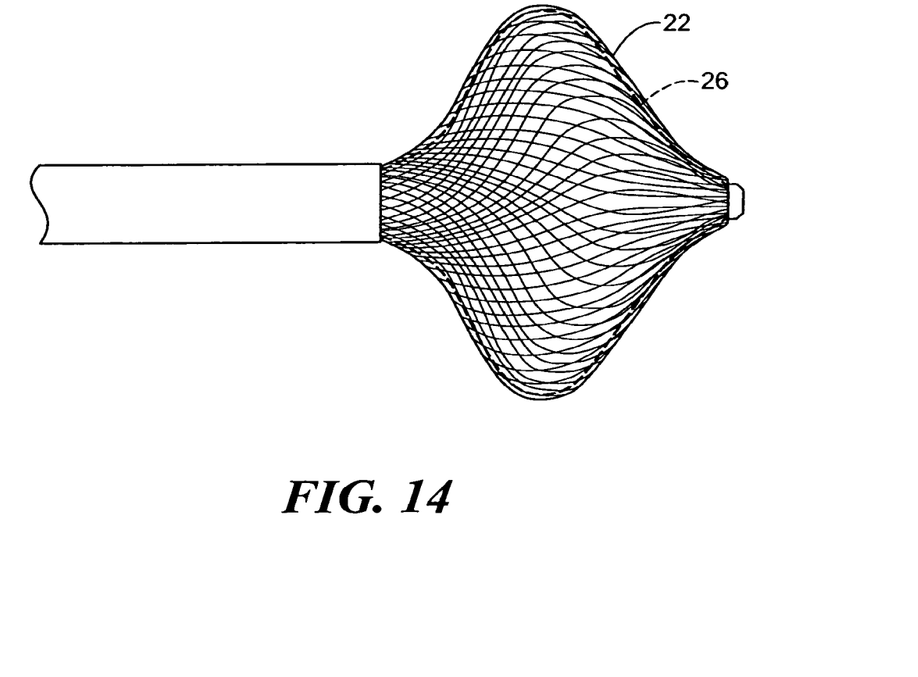
FIG. 14 depicts an additional geometric configuration of an embodiment of a medical device in accordance with the present invention.

Now referring to FIGS. 1 and 2, an embodiment of the present invention provides a medical device 10 defining an elongate body 12 such as a catheter. The elongate body 12 may define a proximal portion and a distal portion, and may further include one or more lumens disposed within the elongate body thereby providing mechanical, electrical, and/or fluid communication between the proximal portion of the elongate body 12 and the distal portion of the elongate body. For example, the elongate body 12 may include an injection lumen 14 and an exhaust lumen defining a fluid flow path therethrough. In addition, the elongate body may include a guidewire lumen 16 extending along at least a portion of the length of the elongate body 12 for over-the-wire applications, where the guidewire lumen 16 may define a proximal end and a distal end. The guidewire lumen 16 may be disposed within the elongate body 12 such that the distal end of the guidewire lumen 16 extends beyond the and out of the distal portion of the elongate body 12.

The elongate body 12 may further include a deflection mechanism whereby the elongate body and components coupled thereto may be maneuvered in one or more planes of motion. For example, a pull wire with a proximal end and a distal end may have its distal end anchored to the elongate body at or near the distal end. The proximal end of the pull wire may be anchored to a knob or lever 18 controllable and responsive to an input from an operator or physician.

The medical device 10 of the present invention may include a tip portion 20 towards the distal portion of the elongate body 12, which may be coupled to a portion of the guidewire lumen 16. For example, the tip portion 20 may circumscribe a portion of the distal end of the guidewire lumen 16. The tip portion 20 may define a cavity in fluid communication with the injection lumen 14, yet be isolated from fluid communication with the guidewire lumen 16, i.e., the tip portion 20 may be able to receive a fluid therein while the guidewire lumen 16 remains excluded from any fluid flow originating and/or flowing through the elongate body 12 of the catheter. Accordingly, the tip portion 20 may be able to receive a fluid flow, such as a coolant, thereby allowing the tip portion 20 to thermally affect a desired tissue region and/or to create a spot lesion or focalized ablative pattern.

The medical device 10 of the present invention may further include a shaping element 22 coupled to the distal portion of the elongate body 12 that is configurable into a plurality of geometric configurations, such as those shown in FIGS. 3-14. The shaping element 22 may define a mesh or wire structure, and may be constructed from a combination of elastic materials, non-elastic materials, and/or shape-memory materials, such as a nickel-titanium alloy or the like, for example. As used herein, the term "mesh" is intended to include any element having an openwork fabric or structure, and may include but is not limited to, an interconnected network of wire-like segments, a sheet of material having numerous apertures and/or portions of material removed, or the like. A particular geometric configuration of the shaping element 22 may be achieved through the application of mechanical force, thermal energy, and/or electrical energy. For example, the shaping element 22 may be predisposed and/or biased towards a first geometric configuration, which may include a substantially elongated, cylindrical shape. Upon the application of a particular mechanical, thermal, and/or electrical force, the shaping element 22 may be selectively transitioned from the first geometric configuration to a second geometric configuration, having a substantially spherical shape, for example.

As discussed, the transition from a first particular configuration to a second particular configuration of the shaping element 22 may be achieved by the application of mechanical, thermal, or electrical forces. Further, the transition may be a result of particular material properties exhibited by the construction of the shaping element 22. For example, the shaping element 22 may include a mesh structure including components made from a shape-memory material, as well as components made from a relatively non-elastic material. The components made from the shape-memory material may be predisposed and/or biased towards a first geometric configuration, while the non-elastic components may be predisposed and/or biased towards a second geometric configuration. When the shaping element 22 is placed under a first thermal condition, such a temperature range between 10° C. to 40° C., the shape-memory material may be dominant over the non-elastic components, causing the shaping element 22 to retain the first geometric configuration. When subjected to a second thermal condition, between −100° C. and 10° C. for example, the shape-memory components may become increasingly pliable, thereby allowing the non-elastic components to dominate and causing the shaping element 22 to assume the second geometric configuration.

Figure 15:
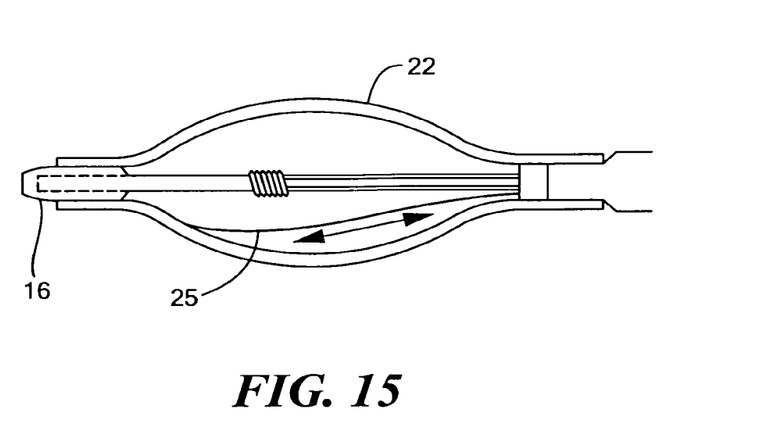
FIG. 15 illustrates an embodiment of a medical device in accordance with the present invention.
Figure 16:
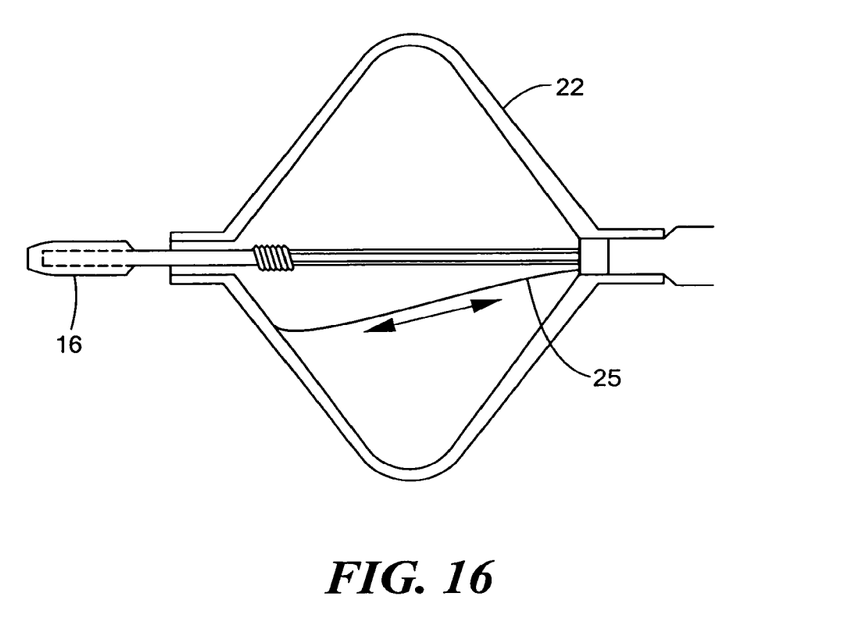
FIG. 16 shows an embodiment of a medical device in accordance with the present invention.

An additional example of a shaping element 22 being configurable into multiple geometric configurations may include a shaping element 22 constructed from a single material being predisposed and/or biased towards a first geometric configuration. However, the medical device of the present invention may include an actuator element 24 that may impart a mechanical force on the shaping element 22 and/or a component coupled thereto to overcome the predisposition of the shaping element 22 to retain the first geometric configuration. As shown in FIGS. 1 and 2, the actuator element 24 may include a pull wire or the like affixed to a portion of the shaping element 22 and/or portions of the medical device in proximity to the shaping element, such as the guidewire lumen 16. For example, a portion of the shaping element 22 may be coupled to a portion of the movable guidewire lumen 16. Upon manipulation of the actuator element 24, the guidewire lumen 16 may be longitudinally moved in a proximal direction, whereby the predisposed first geometric configuration of the shaping element 22 is attained. However, the guidewire lumen 16 may then be moved in a distal direction, thereby tensioning the shaping element 22 in order to overcome the bias of the shaping element. As a result, the shaping element 22 attains a second geometric configuration different than the first geometric configuration. Additionally, the actuator element 24 may include a push rod or other mechanical coupling for imparting a mechanical and/or physical force on the shaping element 22 to overcome and thereby dominate the first geometric configuration that the shaping element 22 may be predisposed to provide. For example, as shown in FIGS. 15 and 16, a pull wire 25 may be coupled to a portion of the shaping element 22 for tensioning and/or loosening of the shaping element 22 during a procedure. Moreover, the shaping element 22 may be slideably disposed about the guidewire lumen 16 such that the guidewire lumen 16 remains in place while the shaping element 22 is manipulated into the desired configuration.

In addition to providing desired geometric configurations, the shaping element 22 may be electrically conductive. For example, the shaping element 22 may be used to provide the ability to map electrical properties of a particular tissue region, such as in the heart, whereby an electrocardiogram may be obtained. Further, the shaping element 22 may be used to provide a conductive surface for delivering radiofrequency energy to a particular tissue site, and/or to provide the ability to measure a relative impedance and/or resistance for the purpose of fluid leak detection.

The medical device 10 of the present invention may further include an expandable element 26 at least partially disposed on the elongate catheter body 12, and may further be disposed within a portion of the shaping element 22. The expandable element 26 may include a balloon or other expandable structure, which may define a proximal end coupled to the distal portion of the elongate body 12 of the catheter, while further defining a distal end coupled to the tip portion and/or the distal end of the guidewire lumen 16. In addition, the expandable element 26 may have any of a myriad of shapes, and may further include one or more material layers providing for puncture resistance, radiopacity, or the like. The expandable element 26 may be in communication with the fluid injection and exhaust lumens of the medical device as described above, i.e., a fluid flow path may provide an inflation fluid, such as a cryogenic fluid or the like, to the interior of the expandable element 26. The expandable element 26 may be inflated within the shaping element 22, thereby conforming to the shape of the shaping element 22. As such, irrespective of whether the expandable element 26 has a particular shape or dimensional capacity, the shaping element 22 may be used to provide a guide and/or "shell" within which the expandable element 26 may be inflated to ensure a desired geometric configuration and/or a desired volume.

The shaping element 22 may, therefore, limit certain portions of the expandable element 26 from expanding, while other areas or regions of the expandable element 26 may be stretched. As portions of the expandable element 26 are stretched, the particular thermal properties of that region may change, i.e., the stretched portions may more readily conduct thermal energy than portions of the expandable element 26 that have not been stretched to the same extent, if at all. Accordingly, the shaping element 22 may provide a particular shape or geometric configuration in which particular areas of the expandable element 26 are allowed to stretch to thereby conduct heat more readily, while other portions of the expandable element 26 are not stretched to provide a degree of thermal insulation. As a result, the shaping element 22 and thus the expandable element 26 may be configured to provide varying thermal conductivity to different regions of tissue while the medical device 10 remains in a fixed position.

In an exemplary system, the medical device of the present invention may be coupled to a console 28, which may contain a fluid supply and exhaust, as well as various control mechanisms for operation of the medical device 10.

An exemplary use of the medical device 10 of the present invention may include making multiple ablative lesions having varying geometric shapes and/or dimensions on a desired tissue region. In such a procedure, the distal portion of the medical device 10 may be positioned in proximity to a tissue region to be treated. Primarily, the tip portion 20 of the medical device 10 may be subjected to a fluid flow, including a cryogenic coolant or the like, to create a focalized and/or spot lesion within a desired tissue region. Additionally, the shaping element 22 of the medical device 10 may be in a first geometric configuration, such as an elongated cylindrical shape, for example. Subsequently, a fluid, such as a cryogenic coolant, may be used to expand the expandable element 26 such that the expandable element 26 substantially fills the interior cavity defined by the shaping element 22. The expandable element 26 may be inflated such that portions of the expandable element protrude through a mesh construct of the shaping element 22 to contact and/or be in position to thermally affect the desired tissue region, while substantially retaining the geometric configuration of the shaping element 22. While the shaping element 22 ensures the expandable element 26 retains the first geometric configuration, coolant may be circulated through the expandable element 26 in order to thermally affect the tissue region and/or to create a tissue lesion having a desired shape, such as a linear tissue lesion.

Upon achieving the desired effect, the flow of coolant through the expandable element 26 may be discontinued such that the expandable element 26 is at least partially deflated. The medical device 10 may then be repositioned in proximity to a tissue region where additional thermal treatment may be performed. The shaping element 22 may subsequently be transitioned from the first geometric configuration to the second geometric configuration, which may include a substantially spherical shape, for example. The transition may be achieved by imparting a mechanical, thermal, and/or electrical force on the shaping element, and may further include manipulation of the actuator element 24. Once the desired geometric configuration has been achieved, the expandable element 26 may once again be inflated within the shaping element 22, using the aforementioned coolant, for example. Accordingly, the second geometric configuration may be used to impart a second tissue lesion and/or thermally affected area having a varied geometric pattern and/or dimension to that of the first tissue lesion, such as a substantially circular shape, for example. The second geometric configuration may also be used to thermally affect the same tissue region that was affected when the tissue region was treated with the first configuration and/or to create the tissue lesion having a desired shape, such as a substantially circular shape.

Although the exemplary use described above employed first and second geometric configurations, it is contemplated that a shaping element capable of more than two configurations may be employed and achieved through a combination of mechanical, thermal, and/or electrical forces, as well as through characteristics provided through material selection in the construction of the shaping element. Moreover, while examples and illustrations of particular geometric configurations have been provided, it is understood that virtually any shapes, configurations, and/or dimensions may be included and/or achieved by the medical device of the present invention, including but not limited to those shapes illustrated and described herein. A particular geometric configuration may include circular, conical, concave, convex, rounded, or flattened features and/or combinations thereof. Accordingly, an embodiment of the medical device of the present invention may be able to provide focal lesions, circular lesions, linear lesions, circumferential lesions, and combinations thereof.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
    an elongate body including a proximal portion, a distal portion, a fluid injection lumen, and a guidewire lumen having a distal tip, the distal tip defining a cavity in fluid communication with the fluid injection lumen;
    an expandable element coupled to the elongate body, the expandable element being in fluid communication with the fluid injection lumen, the expandable element including an interior chamber, the cavity within the distal tip being fluidly isolated from the interior chamber;

a mesh at least partially surrounding the expandable element, the mesh being transitionable between a first geometric configuration having an elongated, substantially cylindrical shape and a second geometric configuration having a substantially cylindrical shape; and an actuator element, the actuator element being able to cause the mesh to transition from the first geometric configuration to the second geometric configuration.

2. The medical device of claim 1, wherein the actuator element is in mechanical communication with the guidewire lumen.

3. A medical device, comprising an elongate body including a proximal portion and a distal portion;

a fluid injection lumen at least partially disposed within elongate body;

a guidewire lumen movably disposed within at least a portion of the elongate body, the guidewire lumen including a proximal end and a distal end;

a tip portion at the distal end of the guidewire lumen, the tip portion defining a cavity that is in fluid communication with the fluid injection lumen;

an expandable element defining a proximal end and a distal end, the proximal end being coupled to the distal portion of the catheter body and the distal end being coupled to the tip portion, the expandable element being in fluid communication with the fluid injection lumen and being fluidly isolated from the cavity of the tip portion; and an actuator element in mechanical communication with the guidewire lumen.

4. The medical device of claim 3, further comprising a mesh at least partially surrounding the expandable element, the mesh being selectively transitionable between a first geometric configuration and a second geometric configuration.

5. The medical device of claim 4, wherein the first geometric configuration includes an elongated, substantially cylindrical shape and the second geometric configuration includes a substantially spherical shape.

6. The medical device of claim 4, wherein the mesh is coupled to the guidewire lumen.

7. The medical device of claim 6, wherein movement of the actuator element causes a corresponding movement of the guidewire lumen to transition the expandable element between the first geometric configuration and the second geometric configuration.

8. A method for thermally affecting a tissue region, comprising the steps of:

positioning a medical device proximate to the tissue region, the medical device including a shaping element that is selectively transitionable between a first geometric configuration and a second geometric configuration, and an expandable element that is disposed within the shaping element, the shaping element being in the first geometric configuration;

directing a coolant into the expandable element to reduce a temperature of the expandable element;

thermally affecting the tissue region with the expandable element, the shaping element being in the first geometric configuration;

transitioning the shaping element to the second geometric configuration; and thermally affecting the tissue region with the expandable element, the shaping element being in the second geometric configuration.

9. The method of claim 8, wherein the medical device further includes an actuator element coupled to the shaping element for manipulation thereof, and wherein the step of configuring the shaping element into the second geometric configuration includes manipulating the actuator element.

10. The method of claim 9, wherein the actuator element includes a pull wire coupled to the shaping element.

11. The method of claim 9, wherein the shaping element defines a braided mesh including a plurality of elastic components biased toward only the first geometric configuration and a plurality of non-elastic components biased toward only the second geometric configuration.

12. The method of claim 11, wherein the plurality of elastic components are constructed at least in part from a thermally affected shape memory material.

13. The method of claim 11, wherein a mechanical force exerted by the actuator element transitions the shaping element between the first geometric configuration and the second geometric configuration.

14. The method of claim 8, wherein the tissue region includes cardiac tissue.

* * * * *